United States Patent
Fukuda et al.

(10) Patent No.: US 7,964,222 B2
(45) Date of Patent: Jun. 21, 2011

(54) AQUEOUS EXTERNAL PREPARATION FOR SCALP

(75) Inventors: Reiko Fukuda, Tokyo (JP); Hideshi Kidena, Chiba (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/021,768

(22) Filed: Jan. 29, 2008

(65) Prior Publication Data

US 2008/0181976 A1    Jul. 31, 2008

(30) Foreign Application Priority Data

Jan. 30, 2007    (JP) ................................. 2007-019420

(51) Int. Cl.
*A61K 36/00* (2006.01)
*A61K 36/61* (2006.01)
*A61K 8/00* (2006.01)
*A61K 8/18* (2006.01)
*A61K 36/48* (2006.01)

(52) U.S. Cl. ........ 424/725; 424/742; 424/757; 424/70.1
(58) Field of Classification Search ........................ None
See application file for complete search history.

(56) References Cited

U.S. PATENT DOCUMENTS

2004/0228824 A1    11/2004    Voigt

FOREIGN PATENT DOCUMENTS

| EP | 0 640 333 | | | 3/1995 |
|---|---|---|---|---|
| JP | 2000-206043 | | | 7/2000 |
| JP | 2000-206044 | | | 7/2000 |
| JP | 2001-2532 | | | 1/2001 |
| JP | 2001002532 | A | * | 1/2001 |
| JP | 2005-206536 | | | 4/2005 |
| JP | 2005-126347 | | | 5/2005 |
| JP | 2005206539 | A | * | 8/2005 |
| JP | 2006-143640 | | | 6/2006 |
| WO | WO 0040212 | A1 | * | 7/2000 |
| WO | WO 01/30311 | | | 5/2001 |
| WO | WO 0174310 | A2 | * | 10/2001 |

OTHER PUBLICATIONS

Mori et al, Direct determination of effective ingredients in aerosol hair growers, Journal of Health Science 45 (5) 289-292 (1999).*
News Releases Taisho Pharmaceutical co., [on line[ Jun. 19, 2002, XP002520817 retrieved from the Internet: URL: http://taisho/co.jp/en company/release/2002/061902-e-htm.
Database WPI, Thomson Scientific. London, GB/ AN 2005-376691 XP-002520818.
Database WPI, Thomson London, GB/AN 2005-558358 XP-002520819.
Database WPI, Thomson Scientific London, GB/AN 2006/387310 XP-002520820.

* cited by examiner

*Primary Examiner* — Qiuwen Mi
(74) *Attorney, Agent, or Firm* — Oblon, Spivak, McClelland, Maier & Neustadt, L.L.P.

(57) ABSTRACT

An aqueous external preparation for scalp, that is directly applied to the scalp to improve the elasticity and luster of newly grown or growing hair without affecting the safety or the feeling of touch of the hair, contains the following components (a) a eucalyptus extract; (b) a blood flow enhancer; (c) an anti-inflammatory agent; (d) an acrylic acid/C10-30 alkyl acrylate copolymer; and (e) ethanol. The blood flow enhancer (b) is preferably selected from the group consisting of *swertia japonica* extract, vitamin E, nicotinic acid and derivatives thereof. The anti-inflammatory agent (c) is preferably glycyrrhetin or derivatives thereof.

5 Claims, No Drawings

AQUEOUS EXTERNAL PREPARATION FOR SCALP

BACKGROUND OF THE INVENTION

1. Field of the Invention

The present invention relates to an aqueous external preparation for scalp that can improve the elasticity of hair and enhance the luster of hair.

2. Background Art

Many scalp preparations have been proposed thus far that contain synthetic ingredients or natural extracts with various effects for the purpose of preventing the decrease in the hair growth area of the scalp and further recovering the hair growth area that has already been decreased. Examples thereof include a hair growth formula containing a blood flow enhancer or a follicle stimulator and a polar solvent extract of eucalyptus plant (JP-A-2001-2532), and a hair restoration/hair growth formula containing flavanonols, a eucalyptus extract and menthol (JP-A-2006-143640).

With regard to the effects of conventional hair restoration/hair growth products, the elasticity and luster of newly grown or growing hair are attracting much attention. The loss of the elasticity and luster of hair is a phenomenon seen not only in people with less hair, but also in people with a normal hair volume as a result of aging. There is an increasing demand among the people to improve the elasticity and luster of their newly grown or growing hair.

However, most of conventional hair restoration/hair growth products, including those described prior art documents, have been developed with the intention of facilitating hair restoration/hair growth without affecting the safety and feeling of touch of hair. At present, the demand for techniques that can improve the elasticity and luster of hair is left unsatisfied. Thus, no products are available that can improve the elasticity and luster of hair.

DISCLOSURE OF THE INVENTION

Accordingly, it is an object of the present invention to provide an external preparation that is directly applied to the scalp to improve the elasticity and luster of newly grown or growing hair without sacrificing the safety and the feeling of touch of hair.

The present inventors have found that a novel aqueous external preparation for scalp containing a eucalyptus extract, a blood flow enhancer, an anti-inflammatory agent, a particular thickener, and ethanol can achieve the above-described object, and attained the present invention.

The present invention provides an aqueous external preparation for scalp containing water and the following components (a) through (e):

(a) a eucalyptus extract;
(b) a blood flow enhancer;
(c) an anti-inflammatory agent;
(d) an acrylic acid/C10-30 alkyl acrylate copolymer; and
(e) ethanol.

Because of containing the components (a) through (e), the aqueous external preparation for scalp of the present invention can be directly applied to the scalp to allow these components to penetrate into the scalp where they synergically act on the hair roots, thus improving the elasticity of newly grown or growing hair and also enhancing the luster thereof without sacrificing the safety and the feeling of touch of the hair.

DETAILED DESCRIPTION OF THE INVENTION

The aqueous external preparation for scalp of the present invention is composed of at least water, (a) a eucalyptus extract, (b) a blood flow enhancer, (c) an anti-inflammatory agent, (d) an acrylic acid/C10-30 alkyl acrylate copolymer, and (e) ethanol. It acts to improve the elasticity of newly grown or growing hair and also enhance the luster thereof.

The "elasticity", the property of hair that can be improved by the aqueous external preparation for scalp of the present invention, is closely related to the hardness of hair. A harder hair gives more elastic feeling, whereas a less hard hair gives less elastic feeling. The hardness of hair can be evaluated by the Young's modulus. A hair with a greater modulus can be determined as hard, whereas a hair with a smaller modulus can be determined as soft. Thus, the Young's modulus serves as an appropriate measure of the elasticity of hair.

The Young's modulus of a single hair can be determined by the equation (1) shown below. The diameter of a hair can be measured by a common laser thickness meter (available from manufacturers such as Dia-Stron Limited and Kato Tech Co., Ltd.). The bending stress of a hair can be measured by a common bending stress meter (available from manufacturers such as Dia-Stron Limited and Kato Tech Co., Ltd.).

$$M/(1/\rho) = E \times I \quad (1)$$

The variables and coefficients in the equation (1) are as follows:

M: bending stress [gf·cm]
$1/\rho$: curvature
E: Young's modulus [GPa]
$I = \pi a b^3 / 64$
a: longer diameter of hair [μm]
b: shorter diameter of hair [μm]

The luster of hair can be determined, for example, by a simple luster analyzer described in JP-A-2000-206043 or JP-A-2000-206044. In such a case, hair may be irradiated with light from a light source and the relative regular reflection is measured as an index of hair luster.

A eucalyptus extract, the component (a) of the aqueous external preparation for scalp of the present invention, is obtained from Eucalyptus globules, a plant species belonging to the genus Eucalyptus of the Myrtle family. Preferably, the extract is obtained directly from leaves, branches or other plant parts, or by drying and crushing these parts, followed by extraction with a solvent and concentration. The extract is known to have various effects, including moisturizing effects, antimicrobial effects, bactericidal effects, blood flow-enhancing effects and astringent effects. The component (a) may be a commercial product of eucalyptus extract. The solvent used for extraction may be any solvent commonly used to extract plant materials, including water, petroleum ether, n-hexane, toluene, dichloroethane, chloroform, diethyl ether, ethyl acetate, acetone, methanol, ethanol, propanol, butanol, ethylene glycol, propylene glycol and butylene glycol and the like. Of these, water, ethanol, propylene glycol and butylene glycol are particularly preferred. The solvents may be used in combination of two or more. Eucalyptus may be extracted by conventional techniques. For example, the plant may be immersed in the extraction solvent at 3 to 100° C. for several hours to several weeks, or the extraction solvent may be heated and refluxed.

While the eucalyptus extract may be used directly as an active ingredient in the external preparation of the present invention, it may be subjected to a proper separation technique, such as gel filtration, chromatography and precision distillation, to separate and utilize more active fractions.

The amount of the eucalyptus extract of the component (a) in the aqueous external preparation for scalp is preferably in the range of 0.00001 to 1% by weight (in terms of solid components), more preferably in the range of 0.0001 to 0.1% by weight, and even more preferably in the range of 0.001 to 0.05% by weight with respect to the entire amount of the aqueous external preparation for scalp.

The blood flow enhancer, the component (b) of the aqueous external preparation for scalp of the present invention, may be a swertia japonica extract, vitamin E and derivatives thereof (such as DL-α-tocopherol, D-α-tocopherol, DL-α-tocopherol acetate and D-α-tocopherol acetate), nicotinic acid and derivatives thereof (such as nicotinic acid, DL-α-tocopherol nicotinate, nicotinamide and benzyl nicotinate) or the like. Of these, nicotinamide and swertia japonica extract are particularly preferred because of their favorable effects. Two or more blood flow enhancers may be used in combination.

The amount of the blood flow enhancer of the component (b) in the aqueous external preparation for scalp is preferably in the range of 0.00001 to 10% by weight, more preferably in the range of 0.0001 to 7% by weight, and even more preferably in the range of 0.001 to 5% by weight with respect to the entire amount of the aqueous external preparation for scalp; the amount may vary depending on the type of the blood flow enhancer. By using the blood flow enhancer in the specified range, the advantageous effects of the present invention can be further enhanced. More specifically, when the component (b) is a swertia japonica extract, its amount is preferably in the range of 0.00001 to 1% by weight (as the solid components after evaporation), more preferably in the range of 0.0001 to 0.1% by weight, and even more preferably in the range of 0.001 to 0.05% by weight. When the component (b) is vitamin E or nicotinic acid or derivatives thereof, its amount is preferably in the range of 0.0001 to 3% by weight, more preferably in the range of 0.001 to 1% by weight, and even more preferably in the range of 0.01 to 0.5% by weight.

The anti-inflammatory agent, the component (c) of the aqueous external preparation for scalp of the present invention, is preferably glycyrrhetin or derivatives thereof, such as glycyrrhizic acid or derivatives thereof and glycyrrhetinic acid or derivative thereof. Of these compounds, dipotassium glycyrrhizinate and β-glycyrrhetinic acid are particularly preferred because of their favorable effects. Two or more anti-inflammatory agents may be used in combination.

The amount of the anti-inflammatory agent of the component (c) in the aqueous external preparation for scalp is preferably in the range of 0.0001 to 5% by weight, more preferably in the range of 0.001 to 1% by weight, and even more preferably in the range of 0.01 to 0.5% by weight with respect to the entire amount of the aqueous external preparation for scalp. By using the anti-inflammatory agent in the specified range, the advantageous effects of the present invention can be further enhanced.

The acrylic acid/C10-30 alkyl acrylate copolymer, the component (d) of the aqueous external preparation for scalp of the present invention, is a copolymer obtained by copolymerization of a C10-30 alkyl acrylate with acrylic acid, methacrylic acid, or a simple acrylate or methacrylate crosslinked by sucrose allyl ether or pentaerythritol allyl ether. This type of copolymer is commonly used as a thickener or an emulsion dispersing agent.

The acrylic acid/C10-30 alkyl acrylate copolymer of the component (d) as explained above indicates a preferable thickening behavior even in an aqueous composition containing ethanol in a relatively large amount. The composition develops better improvement in Young's modulus and luster of the hair, as compared to the case where such an aqueous composition is not thickened. The above improvement in Young's modulus and luster of the hair obtained by using the acrylic acid/C10-30 alkyl acrylate copolymer is not obtained in the case of using a carboxyvinyl polymer (trade name; CARBOPOL), which is a conventional thickening polymer.

Specific examples of the acrylic acid/C10-30 alkyl acrylate copolymer of the component (d) is preferably PEMULEN TR-1 and PEMULEN TR-2 (products of Goodrich Corp.). They are used as the thickening agent having an emulsifying effect in the field of an external preparation for skin.

In the present invention, it is preferable to form an aqueous gel by neutralizing the acrylic acid/C10-30 alkyl acrylate copolymer of the component (d). In this case, a basic compound may be added to the aqueous external preparation for scalp. Basic compounds includes, for example, organic amines such as triethanolamine, monoethanolamine, and 2-amino-2-methyl-1-propanol; inorganic bases such as ammonia, potassium hydroxide, and sodium hydroxide.

The amount of the above basic compounds is properly determined according to the type of the compounds which is sufficient for forming the aqueous gel by neutralizing the acrylic acid/C10-30 alkyl acrylate copolymer of the component (d).

The amount of the acrylic acid/C10-30 alkyl acrylate copolymer of the component (d) in the aqueous external preparation for scalp is preferably in the range of 0.001 to 3% by weight, more preferably in the range of 0.005 to 2% by weight, and even more preferably in the range of 0.01 to 1% by weight with respect to the entire amount of the aqueous external preparation for scalp. By using the acrylic acid/C10-30 alkyl acrylate copolymer in the specified range, the advantageous effects of the present invention can be further enhanced.

Ethanol of the component (e) constituting the aqueous external preparation for scalp is used preferably in the range of 20 to 60% by weight, more preferably in the range of 23 to 40% by weight, and even more preferably in the range of 25 to 35% by weight with respect to the entire amount of the aqueous external preparation for scalp. By using ethanol in the specified range, the advantageous effects of the present invention can be further enhanced.

The content of water which is used as a medium of the aqueous external preparation for scalp of the present invention is preferably 30 to 75% by weight, more preferably 50 to 73% by weight, and even more preferably 55 to 70% by weight. Water for use in the aqueous external preparation for scalp is preferably ion-exchanged water, purified water or distilled water.

When necessary, the aqueous external preparation for scalp of the present invention may further contain at least one or more components selected from the group of antimicrobial agents, follicle stimulators, humectants, kelatolytic agents, antiseborrheic agents, local stimulators, anti-androgen agents, potassium channel openers and antioxidants. The amount of these ingredients in the aqueous external preparation for scalp of the present invention is preferably in the range of 0.001 to 30% by weight, and more preferably in the range of 0.01 to 15% by weight. By using these ingredients in the specified range, the advantageous effects of the present invention can be further enhanced.

Examples of the antimicrobial agent include isopropylmethyl phenol, benzalconium chloride, octopirox, photosensitive dye 101, photosensitive dye 201, chlorohexidine, salicylic acid, zinc pyrithione, potassium sorbate, hinokitiol and phenol and the like. Of these, isopropylmethyl phenol, benzalconium chloride, octopirox, zinc pyrithione and hinokitiol are particularly preferred.

Examples of the follicle stimulator include trans-3,4'-dimethyl-3-hydroxyflavanone, adenosine, pantothenyl ethyl ether, cytopurine, N-acetyl-L-methionine, *Stephania cepharantha*, cepharanthine, disodium adenosine triphosphate, potassium aspartate, photosensitive dye 301, pentadecanoic glyceride, ethyl pantothenate, Panacls Japonici Rhizoma, biotin, sodium mononitroguayacol, yeast extracts, garlic, pearl protein extract, jujube extract, placenta extract, royal jelly, *sophora* extract paste (kujin), 6-benzylaminopurine and dialkyl monoamine derivatives and the like. Of these, *Stephania cepharantha*, cepharanthine, disodium adenosine triphosphate, pentadecanoic glyceride, ethyl pantothenate, Panacls Japonici Rhizoma, biotin, sodium mononitroguayacol, placenta extract and royal jelly are particularly preferred.

Examples of the humectant include *hypericum erectum* extract, oat extract, soluble collagen, glycerol, chondroitin sulfate, tuberose polysaccharides, propylene glycol, *Cordyceps sinensis* extract, *Plectranthus japonicus* extract, barley extract, orange extract, grape extract, seaweed extract, *Moutan cortex* extract, *Rehmannia glutinosa* extract, duke extract, *Rosa rugosa* extract, extract of *Coix lacryma-jobi* var.

*ma-yuen, Panax ginseng* extract, delamide (decyltetradecyldimethylamine oxide), *Althaea officinalis* extract, quachalalate extract, comfrey extract, coriander extract, Japanese pepper extract, *Hydrangea serrata* extract and hop extract and the like. Of these, hypericum erectum extract, oat extract, glycerol, tuberose polysaccharides, *Cordyceps sinensis* extract, *Plectranthus japonicus* extract, barley extract, grape extract, seaweed extract, *Moutan cortex* extract, *Rehmannia glutinosa* extract, duke extract, *Rosa rugosa* extract and extract of *Coix lacryma-jobi* var. *ma-yuen* are particularly preferred.

Examples of the kelatolytic agent include aspirin and the like. Examples of the antiseborrheic agent include sulfur, lecithin, *Polygoni multiflori* radix extract and tioxolone and the like.

Examples of the local stimulator include camphor, capsicum tincture, 1-menthol, nonylic acid vanillyl amide, ginger tincture, Holland mustard extract, cantharis tincture, zanthoxylum fruit extract, mentha herb oil and horseradish extract and the like. Examples of the anti-androgen agent include cyproterone acetate, 11-α-hydroxyprogesterone, flutamide, 3-deoxyadenosine, chlormadinone acetate, ethinyl estradiol, spironolactone, epitesterone, aloe, *Zanthoxylum* fruit and *Panax ginseng* and the like.

Examples of the potassium channel opener include minoxidil, chromakalim, diazoxide and derivatives thereof and pinacidil and the like.

Examples of the antioxidant include tea extract, green tea extract, clove extract, rose fruit extract, *Chrysolepsis* extract, vitamin C and derivatives thereof, erythorbic acid, propyl gallate and dibutylhydroxytoluene and the like.

The aqueous external preparation for scalp of the present invention may further contain at least one or more surfactants selected from nonionic surfactants, cationic surfactants, anionic surfactants and amphoteric surfactants. The surfactant may be any surfactant commonly used in cosmetic products. Examples of the nonionic surfactant include polyoxyethylene alkyl ethers, polyoxyethylene alkyl aryl ethers, polyoxyethylene fatty acid esters, polyoxyethylene hydrogenated castor oil, polyoxyethylene sorbitan fatty acid esters and polyoxyethylene sorbitol fatty acid esters and the like. Examples of the cationic surfactant include alkylamine salts and quaternary ammonium salts and the like. Examples of the anionic surfactant include lauryl sulfates, polyoxyethylene lauryl ether sulfates and the like. Examples of the amphoteric surfactant include alkyl betaines and amine oxides and the like.

The amount of the surfactant in the aqueous external preparation for scalp of the present invention is preferably in the range of 0.005 to 20% by weight, and more preferably in the range of 0.01 to 10% by weight, with respect to the entire amount of the aqueous external preparation for scalp. By using the surfactant in the specified range, the advantageous effects of the present invention can be further enhanced.

The aqueous external preparation for scalp of the present invention can be produced by common techniques. For example, the above-described components (a) through (e) and water, along with other ingredients, are uniformly mixed together using a common technique.

The aqueous external preparation for scalp of the present invention can be used as a cosmetic product, a pharmaceutical product or a quasi drug depending on the other ingredients or the dosage form. The aqueous external preparation for scalp may be formulated in any suitable dosage form as long as it can be applied to scalp. The dosage form includes lotion, tonic, cream, gel, foam, spray and aerosol and the like. When it is formulated as an aerosol preparation containing a propellant, the propellant may be carbon dioxide, LPG, dimethylether, nitrogen gas, isopentane and nitrous oxide and the like. The propellants may be used either individually or in combination of two or more. Of these, carbon dioxide is particularly preferred because of the favorable feeling it provides during use.

The aqueous external preparation for scalp of the present invention can be used in any suitable fashion as long as the preparation is adhered to the scalp.

EXAMPLES

The present invention will now be described in more detail with reference to Examples and Comparative Examples, which are not intended to limit the scope of the invention in any way.

Example 1 and Comparative Example 1 to 4

Aqueous external preparations for scalp having the compositions shown in Table 1 were prepared by uniformly mixing the respective components. A unit for the amounts in the table 1 is in "% by weight".

3 g of each aqueous external preparation for scalp was applied to the scalp of each of 5 subjects (40 to 45-year-old Japanese females) twice a day. This application had been repeated for three months. Hair samples were collected at the beginning and after a 3-month application period by cutting hair at the root. The thickness and bending stress of each hair were measured. The thickness thereof was measured by a laser thickness meter (available from Kato Tech Co., Ltd.). The bending stress thereof was measured by a bending stress meter (Kato Tech Co., Ltd.) and Young's modulus was determined using the above-described equation (1). Young's modulus obtained after the 3-month application period was divided by that obtained at the beginning of the application period. The results (Ratio of Young's modulus) are shown in Table 1.

The hair samples obtained at the beginning and after the 3-month application period were each analyzed for the intensity of luster using a hair luster analyzer described in JP-A-2000-206044 (see FIGS. 1 to 3, paragraphs 0006 to 0019 and 0026). Specifically, according to the evaluation method described in the same document (see paragraphs 0020 to 0024 and 0027), a luminance distribution curve was obtained. It was differentiated to determine the change in the luminance. The intensity of hair luster was then determined as the absolute value of the luminance change. The hair luster intensity obtained after the 3-month application period was divided by that obtained at the beginning of the application period. The results (ratio of hair luster intensity) are shown in Table 1.

TABLE 1

| | 1 Ex. | Com. Ex. | | | |
|---|---|---|---|---|---|
| Ingredient | 1 | 1 | 2 | 3 | 4 |
| (a) *Eucalyptus* extract (Maruzen Pharmaceuticals Co., Ltd.) | 3.00 | — | — | — | — |
| (b) *Swertia japonica* extract (Ichimaru Pharcos Co., Ltd.) | 1.00 | 1.00 | 1.00 | — | — |
| (b) Nicotinamide (DSM Nutrition Japan K. K.) | 0.10 | 0.10 | — | 0.10 | — |
| (c) Dipotassium glycyrrhizinate (Nippon Paper Chemicals) | 0.15 | 0.15 | 0.10 | — | — |
| (d) PEMULEN TR-2 (BF Goodrich Company) | 0.30 | — | — | — | 0.30 |
| Triethanol amine (Mitsui Chemicals, Inc.) | 0.25 | — | — | — | 0.25 |
| (e) Ethanol (95°) | 30.00 | 30.00 | 30.00 | 30.00 | 30.00 |
| Purified water | bal. | bal. | bal. | bal. | bal. |
| Young's modulus ratio (After 3 months/Initial) | 1.65 | 1 | 0.95 | 0.85 | 0.95 |
| Luster intensity ratio (After 3 months/Initial) | 1.8 | 0.9 | 0.9 | 0.95 | 0.95 |

As can be seen from Table 1, the ratio of Young's modulus and the ratio of hair luster intensity are both significantly greater than 1 in the aqueous external preparation for scalp of Example 1, which contains the components (a) through (e). This indicates that the elasticity and the luster of hair are both significantly improved in the Example 1. In contrast, when any of the components (a) through (d) is lacking, the ratio of Young's modulus and the ratio of hair luster intensity are both less than 1, indicating that neither the elasticity nor the luster of hair has been improved.

Examples 2 to 5, and Comparative Examples 5 to 9

Aqueous external preparations for scalp having a composition shown in Table 2 were prepared by mixing the components uniformly. A unit for the amounts in the table 2 is in % by weight.

1 g of each of the obtained aqueous external preparations for scalp was applied to about 10 cm square area of scalp of each of 3 subjects, two times a day. This application had been repeated for one month. After a 1 month application, the elasticity and the luster of hair were evaluated by three skilled panelists with their eyes and touch, comparing to those at the beginning of the application. The evaluation were carried out by ranking in 4 grades of the following 0 to 3 points. The results were averaged for each scores. The obtained result is shown in Table 2.

| | |
|---|---|
| 3 points | Great improvement is observed. |
| 2 points | Small improvement is observed. |
| 1 point | No improvement is observed. |
| 0 point | Deterioration is observed. |

TABLE 3

| Components | % by weight |
|---|---|
| *Eucalyptus* extract (Maruzen Pharmaceuticals Co., Ltd.) | 3.0 |
| *Swertia japonica* extract (Ichimaru Pharcos Co., Ltd.) | 1.0 |
| Nicotinamide (DSM Nutrition Japan K. K.) | 0.1 |
| Dipotassium glycyrrhizinate (Nippon Paper Chemicals) | 0.1 |
| Peony Extract (Ichimaru Pharcos Co., Ltd.) | 0.2 |
| Pyrocton olamin (Clariant Japan K.K.) | 0.1 |
| DL-α-tocopherol acetate (DSM Nutrition Japan K.K.) | 0.05 |
| Trimethylglycine | 0.03 |
| Rose Water (Ichimaru Pharcos Co., Ltd.) | 0.2 |
| 1-menthol (Takasago International Corp.) | 0.1 |
| Polyoxyethylene (40EO) hydrogenated caster oil (Kao Corp.) | 0.4 |
| Glycerin | 0.2 |
| PEMULEN TR-2 (BF Goodrich Company) | 1.0 |
| 2-amino-2-methyl-1-propanol (Dow Chemical Company) | 0.8 |
| Ethanol | 35.0 |
| Purified water | balance |

Containing specific components (a) through (e), the aqueous external preparation for scalp of the present invention can be directly applied to the scalp to allow these components to penetrate into the scalp where they synergically act on the hair roots, thus improving the elasticity of newly grown or growing hair and also enhancing the luster of hair without affecting the safety or the feeling of touch of the hair. Accordingly, the aqueous external preparation for scalp of the present invention is highly suitable for use in hair cosmetic products or other products that are intended to prevent the loss of, or even improve, the elasticity and the luster of hair caused by aging.

TABLE 2

| | Example | | | | Comparative Example | | | | |
|---|---|---|---|---|---|---|---|---|---|
| Ingredient | 2 | 3 | 4 | 5 | 5 | 6 | 7 | 8 | 9 |
| (a) *Eucalyptus* extract (Maruzen Pharmaceuticals Co., Ltd.) | 3.00 | 3.00 | 3.00 | 3.50 | — | 3.00 | 3.50 | 3.00 | 3.00 |
| (b) *Swertia japonica* extract (Ichimaru Pharcos Co., Ltd.) | 1.00 | 1.00 | — | — | 1.00 | — | 1.00 | 1.00 | 1.00 |
| (b) Nicotinamide (DSM Nutrition Japan K. K.) | 0.10 | — | 0.10 | — | 0.10 | — | 0.10 | 0.10 | 0.10 |
| (b) DL-α-tocopherol acetate (DSM Nutrition Japan K.K.) | — | — | — | 0.10 | — | — | — | — | — |
| (c) Dipotassium glycyrrhizinate (Nippon Paper Chemicals) | 0.15 | 0.10 | — | 0.10 | 0.15 | 0.15 | — | 0.15 | 0.15 |
| (c) β-Glycyrrhizine (Maruzen Pharmaceuticals Co., Ltd.) | — | — | 0.10 | — | — | — | — | — | — |
| (d) PEMULEM TR-2 (BF Goodrich Company) | 0.30 | 0.30 | 0.30 | 0.30 | 0.30 | 0.30 | 0.30 | — | — |
| (e) Ethanol | 30.00 | 30.00 | 30.00 | 30.00 | 30.00 | 30.00 | 30.00 | 30.00 | 30.00 |
| 2-amino-2-methyl-1-propanol (AMP-100, Dow Chemical Company) | 0.25 | 0.25 | 0.25 | 0.25 | 0.25 | 0.25 | 0.25 | — | 0.25 |
| Carbopol 981 (BF Goodrich Company) | — | — | — | — | — | — | — | — | 0.30 |
| Purified water | 65.20 | 65.35 | 66.25 | 65.75 | 68.20 | 66.30 | 64.85 | 65.75 | 65.50 |
| Elasticity of hair | 2.9 | 2.9 | 2.9 | 2.8 | 1.0 | 1.9 | 1.8 | 1.9 | 1.8 |
| Luster of hair | 2.9 | 2.8 | 2.9 | 2.9 | 1.0 | 1.8 | 1.9 | 1.9 | 1.8 |

From table 2, the aqueous external preparations for scalp having the component (a) through (e) show great improvement in the elasticity and the luster of hair. On the contrary, when any of the components (a) through (d) is not used, the elasticity and the luster of hair is not improved.

Example 6

A hair restoration/hair growth formula (gel) having a composition shown in Table 3 was prepared by a conventional way. As in Example 1, the obtained hair restoration/hair growth formula was applied to the scalp of each of 5 subjects (40 to 45-year-old Japanese females). After 3 months, the elasticity and the luster of hair were both significantly improved as compared to the elasticity and the luster prior to application.

What is claimed is:

1. An aqueous external preparation for scalp comprising water and the following components (a) through (e):
   (a) from 0.001 to 0.05% by weight as the solid component of a eucalyptus extract;
   (b) at least one blood flow enhancer selected from the group consisting of the components (i) and (iii), wherein the component (i) is a *swertia japonica* extract and a content of (i) is from 0.001 to 0.05% by weight as the solid component after evaporation, and the component (iii) is at least one of nicotinic acid, DL-α-tocopherol nicotinate, nicotinamide, and benzyl nicotinate, wherein a content of (iii) is from 0.01 to 0.05% by weight;
   (c) from 0.01 to 0.5% by weight of at least one anti-inflammatory agent;

(d) from 0.01 to 1% by weight of at least one copolymer of acrylic acid and C10-30 alkyl acrylate; and (e) from 20 to 60% by weight of ethanol.

2. The aqueous external preparation for scalp according to claim 1, wherein the anti-inflammatory agent (c) is at least one of glycyrrhizic acid and glycyrrhetinic acid.

3. The aqueous external preparation for scalp according to claim 2, wherein the anti-inflammatory agent (c) is at least one of dipotassium glycyrrhizinate and β-glycyrrhetinic acid.

4. The aqueous external preparation for scalp according to claim 1, further comprising at least one additional ingredient selected from the group consisting of antimicrobial agents, follicle stimulators, humectants, keratolytic agents, antiseborrheic agents, local stimulators, anti-androgen agents, potassium channel openers and antioxidants.

5. The aqueous external preparation for scalp according to claim 4, wherein an amount of the at least one additional ingredient is from 0.001 to 30% by weight.

* * * * *